(12) United States Patent
Pacetti

(10) Patent No.: US 8,685,431 B2
(45) Date of Patent: Apr. 1, 2014

(54) BIOLOGICALLY ABSORBABLE COATINGS FOR IMPLANTABLE DEVICES BASED ON COPOLYMERS HAVING ESTER BONDS AND METHODS FOR FABRICATING THE SAME

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 3591 days.

(21) Appl. No.: 10/805,036

(22) Filed: Mar. 16, 2004

(65) Prior Publication Data
US 2005/0208091 A1    Sep. 22, 2005

(51) Int. Cl.
*A61F 2/00* (2006.01)
*C08G 69/26* (2006.01)

(52) U.S. Cl.
USPC ........................... 424/426; 528/332; 528/335

(58) Field of Classification Search
USPC .................................................. 424/423, 497
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. ................... 260/78 |
| 3,773,737 A | 11/1973 | Goodman et al. ............... 260/78 |
| 3,849,514 A | 11/1974 | Gray, Jr. et al. ............... 260/857 |
| 4,226,243 A | 10/1980 | Shalaby et al. ............ 128/335.5 |
| 4,304,767 A | 12/1981 | Heller et al. |
| 4,329,383 A | 5/1982 | Joh ................................ 428/36 |
| 4,343,931 A | 8/1982 | Barrows ........................ 528/291 |
| 4,529,792 A | 7/1985 | Barrows ........................ 528/291 |
| 4,611,051 A | 9/1986 | Hayes et al. ............... 528/295.3 |
| 4,656,242 A | 4/1987 | Swan et al. ................ 528/295.3 |
| 4,733,665 A | 3/1988 | Palmaz |
| 4,760,112 A * | 7/1988 | McCready et al. ............. 525/33 |
| 4,800,882 A | 1/1989 | Gianturco |
| 4,882,168 A | 11/1989 | Casey et al. ................... 424/468 |
| 4,886,062 A | 12/1989 | Wiktor |
| 4,931,287 A | 6/1990 | Bae et al. |
| 4,941,870 A | 7/1990 | Okada et al. .................... 600/36 |
| 4,977,901 A | 12/1990 | Ofstead ........................ 128/772 |
| 5,019,096 A | 5/1991 | Fox, Jr. et al. |
| 5,100,992 A | 3/1992 | Cohn et al. .................... 424/501 |
| 5,112,457 A | 5/1992 | Marchant ...................... 204/165 |
| 5,133,742 A | 7/1992 | Pinchuk ........................... 623/1 |
| 5,163,952 A | 11/1992 | Froix |
| 5,165,919 A | 11/1992 | Sasaki et al. ................... 424/488 |
| 5,219,980 A | 6/1993 | Swidler ......................... 528/272 |
| 5,258,020 A | 11/1993 | Froix |
| 5,272,012 A | 12/1993 | Opolski ..................... 428/423.1 |
| 5,292,516 A | 3/1994 | Viegas et al. .................. 424/423 |
| 5,298,260 A | 3/1994 | Viegas et al. .................. 424/486 |
| 5,300,295 A | 4/1994 | Viegas et al. .................. 424/427 |
| 5,306,501 A | 4/1994 | Viegas et al. .................. 424/423 |
| 5,306,786 A | 4/1994 | Moens et al. .................. 525/437 |
| 5,328,471 A | 7/1994 | Slepian ......................... 604/101 |
| 5,330,768 A | 7/1994 | Park et al. ..................... 424/501 |
| 5,380,299 A | 1/1995 | Fearnot et al. ................. 604/265 |
| 5,417,981 A | 5/1995 | Endo et al. .................... 424/486 |
| 5,447,724 A | 9/1995 | Helmus et al. ................ 424/426 |
| 5,455,040 A | 10/1995 | Marchant ...................... 424/426 |
| 5,462,990 A | 10/1995 | Hubbell et al. ............... 525/54.1 |
| 5,464,650 A | 11/1995 | Berg et al. ...................... 427/2.3 |
| 5,485,496 A | 1/1996 | Lee et al. ......................... 378/64 |
| 5,516,881 A | 5/1996 | Lee et al. ...................... 528/320 |
| 5,569,463 A | 10/1996 | Helmus et al. ................ 424/426 |
| 5,578,073 A | 11/1996 | Haimovich et al. .............. 623/1 |
| 5,581,387 A | 12/1996 | Cahill |
| 5,584,877 A | 12/1996 | Miyake et al. |
| 5,605,696 A | 2/1997 | Eury et al. ..................... 424/423 |
| 5,607,467 A | 3/1997 | Froix |
| 5,609,629 A | 3/1997 | Fearnot et al. ................... 623/1 |
| 5,610,241 A | 3/1997 | Lee et al. ...................... 525/411 |
| 5,616,338 A | 4/1997 | Fox, Jr. et al. |
| 5,624,411 A | 4/1997 | Tuch .............................. 604/265 |
| 5,628,730 A | 5/1997 | Shapland et al. ............... 604/21 |
| 5,644,020 A | 7/1997 | Timmermann et al. ........ 528/288 |
| 5,649,977 A | 7/1997 | Campbell .......................... 623/1 |
| 5,658,995 A | 8/1997 | Kohn et al. .................... 525/432 |
| 5,667,767 A | 9/1997 | Greff et al. ................. 424/9.411 |
| 5,670,558 A | 9/1997 | Onishi et al. .................. 523/112 |
| 5,674,242 A | 10/1997 | Phan et al. |
| 5,679,400 A | 10/1997 | Tuch ............................ 427/2.14 |
| 5,700,286 A | 12/1997 | Tartaglia et al. .................. 623/1 |
| 5,702,754 A | 12/1997 | Zhong .......................... 427/2.12 |
| 5,711,958 A | 1/1998 | Cohn et al. .................... 424/423 |
| 5,716,981 A | 2/1998 | Hunter et al. ................. 514/449 |
| 5,721,131 A | 2/1998 | Rudolph et al. .............. 435/240 |
| 5,723,219 A | 3/1998 | Kolluri et al. |
| 5,735,897 A | 4/1998 | Buirge ............................ 623/12 |

(Continued)

FOREIGN PATENT DOCUMENTS

DE    42 24 401    1/1994
DE    196 52 037    6/1998

(Continued)

OTHER PUBLICATIONS

Nagata Polymer International 1997 42:33-38.*
Bezemer et al. Journal of Biomedical Materials Research 2000 52:8-17.*
Nagata et al. Polymer International 1997 42:33-38.*
International Search Report and Written Opinion of a PCT/US2005/007895, filed Mar. 8, 2005, mailed Sep. 27, 2005.
U.S. Appl. No. 10/718,278, filed Nov. 19, 2003, Hossainy et al.
U.S. Appl. No. 10/719,516, filed Nov. 21, 2003, Tang et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Moreno et al., *Macrophage Infiltration Predicts Restenosis After Coronary Intervention in Patients with Unstable Angina*, Circulation, vol. 94, No. 12, (1996) pp. 3098-3102.

(Continued)

*Primary Examiner* — Juliet C Switzer
*Assistant Examiner* — Caralynne Helm
(74) *Attorney, Agent, or Firm* — Squire Sanders (US) LLP

(57) ABSTRACT

Coatings for an implantable medical device and a method of fabricating thereof are disclosed, and the coatings comprise biologically absorbable poly(ester amides).

3 Claims, No Drawings

(56) References Cited

U.S. PATENT DOCUMENTS

| | | | |
|---|---|---|---|
| 5,746,998 A | 5/1998 | Torchilin et al. | 424/9.4 |
| 5,759,205 A | 6/1998 | Valentini | |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,861,387 A | 1/1999 | Labrie et al. | |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | |
| 5,971,954 A | 10/1999 | Conway et al. | |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,136,333 A | 10/2000 | Cohn et al. | 424/423 |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | |
| 6,180,632 B1 | 1/2001 | Myers et al. | |
| 6,203,551 B1 | 3/2001 | Wu | 606/108 |
| 6,204,353 B1 * | 3/2001 | Eicken et al. | 528/295.3 |
| 6,211,249 B1 | 4/2001 | Cohn et al. | 514/772.1 |
| 6,214,901 B1 | 4/2001 | Chudzik et al. | |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | |
| 6,248,129 B1 | 6/2001 | Froix | |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | |
| 6,395,326 B1 | 5/2002 | Castro et al. | 427/2.24 |
| 6,419,692 B1 | 7/2002 | Yang et al. | 623/1.15 |
| 6,432,543 B2 * | 8/2002 | Harrison et al. | 428/423.1 |
| 6,451,373 B1 | 9/2002 | Hossainy et al. | 427/2.25 |
| 6,482,834 B2 | 11/2002 | Spada et al. | |
| 6,494,862 B1 | 12/2002 | Ray et al. | 604/96.01 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Castro et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,660,810 B1 * | 12/2003 | Ferruti et al. | 525/439 |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,703,040 B2 | 3/2004 | Katsarava et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |

(56) References Cited

U.S. PATENT DOCUMENTS

| | | |
|---|---|---|
| 6,764,505 B1 | 7/2004 | Hossainy et al. |
| 2001/0007083 A1 | 7/2001 | Roorda |
| 2001/0014717 A1 | 8/2001 | Hossainy et al. |
| 2001/0018469 A1 | 8/2001 | Chen et al. ............... 523/121 |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. ......... 623/1.15 |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0015720 A1* | 2/2002 | Katsarava et al. ............ 424/426 |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich ....................... 424/78.37 |
| 2002/0077693 A1 | 6/2002 | Barclay et al. ............... 623/1.13 |
| 2002/0082679 A1 | 6/2002 | Sirhan et al. |
| 2002/0087123 A1 | 7/2002 | Hossainy et al. |
| 2002/0091433 A1 | 7/2002 | Ding et al. ...................... 623/1.2 |
| 2002/0094440 A1 | 7/2002 | Llanos et al. |
| 2002/0111590 A1 | 8/2002 | Davila et al. |
| 2002/0120326 A1* | 8/2002 | Michal ........................ 623/1.15 |
| 2002/0123801 A1 | 9/2002 | Pacetti et al. |
| 2002/0142039 A1 | 10/2002 | Claude |
| 2002/0155212 A1 | 10/2002 | Hossainy ..................... 427/2.25 |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. ..................... 528/310 |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. ................. 623/1.13 |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman .................... 424/486 |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2005/0060028 A1* | 3/2005 | Horres et al. ................. 623/1.38 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| GB | 1365952 A * | 11/1983 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/03218 | 1/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 2003/000308 | 1/2003 |
| WO | WO 2003/022323 | 3/2003 |
| WO | WO 2003/028780 | 4/2003 |
| WO | WO 2003/037223 | 5/2003 |
| WO | WO 2003/039612 | 5/2003 |
| WO | WO 03034944 A1 * | 5/2003 |
| WO | WO 03/080147 | 10/2003 |
| WO | WO 03/082368 | 10/2003 |

(56) References Cited

FOREIGN PATENT DOCUMENTS

| | | |
|---|---|---|
| WO | WO 04/000383 | 12/2003 |
| WO | WO 2004/009145 | 1/2004 |
| WO | WO 2005/061024 | 7/2005 |

OTHER PUBLICATIONS

Oikawa et al., Mechanisms of Acute Gain and Late Lumen Loss After Atherectomy in Different Preintervention Arterial Remodeling Patterns, The Am. J. Of Cardiology, vol. 89, (2002) pp. 505-510.
Scully et al., Effect of a heparan sulphate with high affinity for antithrombin III upon inactivation of thrombin and coagulaton Factor Xa, Biochem J. 262, (1989) pp. 651-658.
Virmani et al., Lessons From Sudden Coronary Death a Comprehensive Morphological Classification Scheme for Atherosclerotic Lesions, Arterioscler Thromb Vasc Biol. (2000) pp. 1262-1275.
U.S. Appl. No. 10/630,250, filed Jul. 30, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/750,139, filed Dec. 30, 2003, DesNoyer et al.
U.S. Appl. No. 10/816,072, filed Mar. 31, 2004, Dugan et al.
U.S. Appl. No. 10/835,656, filed Apr. 30, 2004, Hossainy et al.
U.S. Appl. No. 10/855,294, filed May 26, 2004, Pacetti et al.
Anonymous, Cardiologists Draw—Up the Dream Stent, Clinica 710:15 (Jun. 17, 1996), http://www.dialogweb.com/cgi/document?req=1061848202959, printed Aug. 25, 2003 (2 pages).
Anonymous, Heparin-coated stents cut complications by 30%, Clinica 732:17 (Nov. 18, 1996), http://www.dialogweb.com/cgi/document?req=1061847871753, printed Aug. 25, 2003 (2 pages).
Anonymous, Rolling Therapeutic Agent Loading Device for Therapeutic Agent Delivery or Coated Stent (Abstract 434009), Res. Disclos. pp. 974-975 (Jun. 2000).
Anonymous, Stenting continues to dominate cardiology, Clinica 720:22 (Sep. 2, 1996), http://www.dialogweb.com/cgi/document?reg=1061848017752, printed Aug. 25, 2003 (2 pages).
Aoyagi et al., Preparation of cross-linked aliphatic polyester and application to thermo-responsive material, Journal of Controlled Release 32:87-96 (1994).
Barath et al., Low Dose of Antitumor Agents Prevents Smooth Muscle Cell Proliferation After Endothelial Injury, JACC 13(2): 252A (Abstract) (Feb. 1989).
Barbucci et al., Coating of commercially available materials with a new heparinizable material, J. Biomed. Mater. Res. 25:1259-1274 (Oct. 1991).
Chung et al., Inner core segment design for drug delivery control of thermo-responsive polymeric micelles, Journal of Controlled Release 65:93-103 (2000).
Dev et al., Kinetics of Drug Delivery to the Arterial Wall Via Polyurethane-Coated Removable Nitinol Stent: Comparative Study of Two Drugs, Catheterization and Cardiovascular Diagnosis 34:272-278 (1995).
Dichek et al., Seeding of Intravascular Stents with Genetically Engineered Endothelial Cells, Circ. 80(5):1347-1353 (Nov. 1989).
Eigler et al., Local Arterial Wall Drug Delivery from a Polymer Coated Removable Metallic Stent: Kinetics, Distribution, and Bioactivity of Forskolin, JACC, 4A (701-1), Abstract (Feb. 1994).
Helmus, Overview of Biomedical Materials, MRS Bulletin, pp. 33-38 (Sep. 1991).
Herdeg et al., Antiproliferative Stent Coatings: Taxol and Related Compounds, Semin. Intervent. Cardiol. 3:197-199 (1998).
Huang et al., Biodegradable Polymers Derived from Aminoacids, Macromol. Symp. 144, 7-32 (1999).
ISTC Project G-802, Biodegradable Epoxy-Poly(Ester Amide)s, http://www.tech-db.ru/istc/db/projects.nsf/prjn/G-802 cache, printed May 3, 2004.
Inoue et al., An AB block copolymer of oligo(methyl methacrylate) and poly(acrylic acid) for micellar delivery of hydrophobic drugs, Journal of Controlled Release 51:221-229 (1998).
Kataoka et al., Block copolymer micelles as vehicles for drug delivery, Journal of Controlled Release 24:119-132 (1993).
Katsarava et al., Amino Acid-Based Bioanalogous Polymers. Synthesis and Study of Regular Poly(ester amide)s Based on Bis(α-amino acid)α,μ-Alkylene Diesters and Aliphatic Dicarbolic Acids, Journal of Polymer Science, Part A: Polymer Chemistry, 37(4), 391-407 (1999).
Levy et al., Strategies for Treating Arterial Restenosis Using Polymeric Controlled Release Implants, Biotechnol. Bioact. Polym. [Proc. Am. Chem. Soc. Symp.], pp. 259-268 (1994).
Liu et al., Drug release characteristics of unimolecular polymeric micelles, Journal of Controlled Release 68:167-174 (2000).
Marconi et al., Covalent bonding of heparin to a vinyl copolymer for biomedical applications, Biomaterials 18(12):885-890 (1997).
Matsumaru et al., Embolic Materials For Endovascular Treatment of Cerebral Lesions, J. Biomater. Sci. Polymer Edn 8(7):555-569 (1997).
Miyazaki et al., Antitumor Effect of Implanted Ethylene-Vinyl Alcohol Copolymer Matrices Containing Anticancer Agents on Ehrlich Ascites Carcinoma and P388 Leukemia in Mice, Chem. Pharm. Bull. 33(6) 2490-2498 (1985).
Miyazawa et al., Effects of Pemirolast and Tranilast on Intimal Thickening After Arterial Injury in the Rat, J. Cardiovasc. Pharmacol., pp. 157-162 (1997).
Nordrehaug et al., A novel biocompatible coating applied to coronary stents, European Heart Journal 14, p. 321 (P1694), Abstr. Suppl. (1993).
Ohsawa et al., Preventive Effects of an Antiallergic Drug, Pemirolast Potassium, on Restenosis After Percutaneous Transluminal Coronary Angioplasty, American Heart Journal 136(6):1081-1087 (Dec. 1998).
Ozaki et at., New Stent Technologies, Progress in Cardiovascular Diseases, vol. XXXIX(2):129-140 (Sep./Oct. 1996).
Pechar et al., Poly(ethylene glycol) Multiblock Copolymer as a Carrier of Anti-Cancer Drug Doxorubicin, Bioconjucate Chemistry 11(2):131-139 (Mar./Apr. 2000).
Peng et al., Role of polymers in improving the results of stenting in coronary arteries, Biomaterials 17:685694 (1996).
Saotome, Y., et al., Novel Enzymatically Degradable Polymers Comprising .alpha.-Amino Acid, 1,2-Ethanediol, and Adipic Acid, Chemistry Letters, pp. 21-24, (1991).
Shigeno, Prevention of Cerebrovascular Spasm by Bosentan, Novel Endothelin Receptor, Chemical Abstract 125:212307 (1996).
van Beusekom et al., Coronary stent coatings, Coronary Artery Disease 5(7):590-596 (Jul. 1994).
Wilensky et al., Methods and Devices for Local Drug Delivery in Coronary and Peripheral Arteries, Trends Cardiovasc. Med. 3(5):163-170 (1993).
Yokoyama et al., Characterization of physical entrapment and chemical conjugation of adriamycin in polymeric micelles and their design for in vivo delivery to a solid tumor, Journal of Controlled Release 50:79-92 (1998).

\* cited by examiner

BIOLOGICALLY ABSORBABLE COATINGS FOR IMPLANTABLE DEVICES BASED ON COPOLYMERS HAVING ESTER BONDS AND METHODS FOR FABRICATING THE SAME

BACKGROUND

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

One polymer that can be used for making stent coatings for local drug delivery can be selected from a group of poly(ester amides) described in U.S. Pat. No. 6,503,538 to Chu et al. However, some mechanical properties, such as hardness of the poly(ester amides) taught by Chu et al. may be insufficiently good for stent applications. Accordingly, there is a need to have poly(ester amides) with better properties to allow the poly(ester amides) to be used to make stent coatings for local drug delivery.

SUMMARY

According to one aspect of the present invention, a medical article is provided, the article comprises an implantable substrate having a coating, the coating includes a polymeric product of a reaction between a first reagent, a second reagent, and a third reagent, wherein: (a) the first reagent can be one of the compounds having formulae (1), (2), (3), and (4);

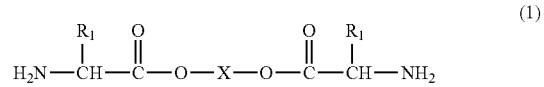

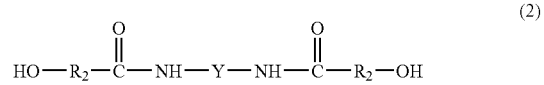

(b) the second reagent can be one of the compounds having formulae (5), (6), (7), and (8);

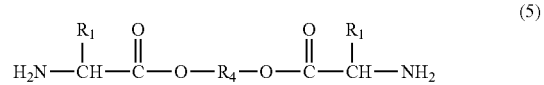

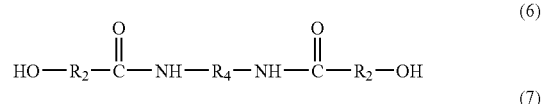

and, (c) the third reagent can be a dicarboxylic acid having the formula (9):

In formulae (1)-(9), $R_1$ can be hydrogen, methyl, iso-propyl, sec-butyl; iso-butyl, or benzyl group; $R_2$ can be methylene, methylmethylene, n-propylene, iso-propylene, ethylmethylene, n-butylene, iso-butylene, sec-butylene, or n-amylene group; $R_3$ can be a straight chained or branched aliphatic alkylene group $C_nH_{2n}$, wherein n is an integer between 2 and 12; $R_4$ can be a moiety derived from a compound selected from a group consisting of poly(ethylene glycol), poly(propylene glycol), random poly(ethylene glycol-co-propylene glycol), poly(ethylene glycol)-block-poly(propylene glycol), hyaluronic acid, poly(2-hydroxyethyl methacrylate), poly(3-hydroxypropylmethacrylamide), poly(styrene sulfonate), poly(vinyl pyrrolidone), and cellulosics; X can be a straight chained or branched aliphatic alkylene group $C_nH_{2n}$, wherein n is an integer between 2 and 12; and Y can be a straight chained or branched aliphatic alkylene group $C_nH_{2n}$, wherein n is 1, 2, or 5.

According to another aspect of the present invention, a medical article is provided. The article comprises an implantable substrate having a coating, and the coating includes a copolymer having a general formula (10) or (11):

$$-[M-P]_m-[M-Q]_n-  \quad (10)$$

$$-[M_1-P]_p-  \quad (11)$$

wherein, M can be a moiety represented by the structure having the formula (12);

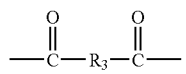
(12)

P can be one of the moieties having the formulae (13), (14), (15), and (16);

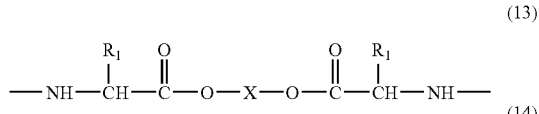
(13)

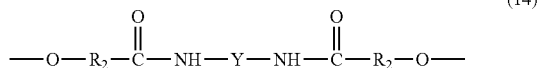
(14)

(15)

(16)

Q can be one of the moieties having the formulae (17), (18), and (19);

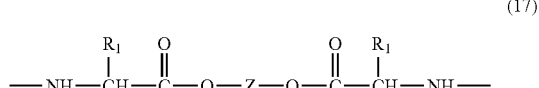
(17)

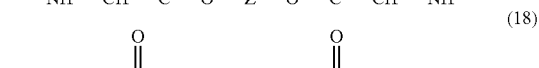
(18)

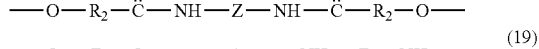
(19)

and $M_1$ can be a moiety represented by the formula (20);

(20)

In formulae (10)-(20), $R_1$ can be hydrogen, methyl, isopropyl, sec-butyl; iso-butyl, or benzyl group; $R_2$ can be methylene, methylmethylene, n-propylene, iso-propylene, ethylmethylene, n-butylene, iso-butylene, sec-butylene, or n-amylene group; $R_3$ can be a straight chained or branched aliphatic alkylene group $C_nH_{2n}$, wherein n is an integer between 2 and 12; X can be a straight chained or branched aliphatic alkylene group $C_nH_{2n}$, wherein n is an integer between 2 and 12; Y can be a straight chained or branched aliphatic alkylene group $C_nH_{2n}$, wherein n is 1, 2, or 5; Z can be a moiety derived from a compound selected from a group consisting of poly(ethylene glycol), poly(propylene glycol), random poly(ethylene glycol-co-propylene glycol), poly(ethylene glycol)-block-poly(propylene glycol), hyaluronic acid, poly(2-hydroxyethyl methacrylate), poly(3-hydroxypropylmethacrylamide), poly(styrene sulfonate), poly(vinyl pyrrolidone), and cellulosics; and m, n, and p can be integers where the value of m is between 5 and 1,800, the value of n is between 1 and 800 and the value of p is between 4 and 1,500.

According to yet another aspect of the current invention, a method for fabricating a medical article is provided, the method includes synthesizing a copolymer and forming a coating based on the copolymer on at least a portion of an implantable substrate, the synthesizing of the copolymer including reacting a first reagent with a second reagent and with a third reagent, wherein: (a) the first reagent can be one of the compounds having formulae (1), (2), (3), and (4); (b) the second reagent can be one of the compounds having formulae (5), (6), (7), and (8); and (c) the third reagent is a dicarboxylic acid having the formula (9), where the formulae (1)-(9) are provided above.

According to yet another aspect of the current invention, a method for fabricating a medical article is provided, the method including synthesizing a copolymer and forming a coating based on the copolymer on at least a portion of an implantable substrate, wherein the copolymer has a general formula (10) or (11), where the formulae (10) and (11) are provided above.

DETAILED DESCRIPTION

1. Terms And Definitions

The following definitions apply:

The term "biologically absorbable" coatings and/or polymers is defined as coatings and/or polymers that are capable of being completely degraded and/or eroded when exposed to bodily fluids such as blood and are gradually resorbed, absorbed and/or eliminated by the body. The processes of breaking down and eventual absorption and elimination of the coating and/or polymer can be caused, for example, by hydrolysis, metabolic processes, bulk or surface erosion, and the like.

Whenever the reference is made to "biologically absorbable" stent coatings and/or polymers forming such stent coatings, it is understood that after the process of degradation, erosion, absorption, and/or resorption has been completed, no coating, in excess of possibly insignificant trace amount, will remain on the stent. In other words, stent coatings and/or polymers forming such stent coatings are considered "biologically absorbable" if the coatings and/or polymers are substantially broken down by the in vivo environment, or by the in vitro environment, such as one having physical, chemical, and/or biological characteristics substantially similar to those of the in vivo environment. An amount of time needed to break down the coatings and/or polymers can be between about 1 day and several years, or between about 1 day and about 24 months; alternatively, between about 2 months and about 18 months; alternatively, between about 3 month and about 12 months.

For purposes of the present invention, "substantially broken down" means that a substantial reduction of the molecular weight of a polymer occurs as a result of the exposure of the polymer to the in vivo environment or to a simulated in vivo environment. The simulated in vivo environment can be the in vitro environment having physical, chemical, and/or biological characteristics that are identical or substantially similar to those of the in vivo environment. Standard analytical techniques normally used by those having ordinary skill in the art can be used to monitor the change of the molecular weight of the polymer. One analytical technique that can be used includes immersing the polymer in a simulated in vivo environment and measuring the loss of the molecular weight of the polymer over time. A number of methods can be used for measuring the molecular weight, for example, gel permeation chromatography (GPC). In some embodiments, if the polymer has lost more than about 10% of its original molecular weight over a 3-month period, then it can be classified as biodegradable.

The term "poly(ester amide)" or "PEA" is defined as a polymer having both at least one ester bond (I) and at least one amide bond (II):

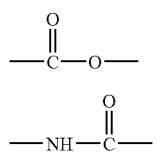

2. Embodiments of the Invention

A coating for an implantable medical device, such as a stent, according to embodiments of the present invention, can be a multi-layer structure that can include the following three layers:

(a) a drug-polymer layer (also referred to as "reservoir" or "reservoir layer"), comprising a polymer and a drug, or alternatively a polymer free drug layer;
(b) an optional primer layer; and/or
(c) an optional topcoat layer.

Each layer of the stent coating can be formed on the stent by dissolving a polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the polymer solution that is applied onto the stent as described above. Alternatively, to fabricate a polymer-free drug layer, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The drug-polymer layer can be applied directly onto at least a part of the stent surface to serve as a reservoir for at least one active agent or a drug which is incorporated into the reservoir layer. The optional primer layer can be applied between the stent and the reservoir to improve the adhesion of the drug-polymer layer to the stent. The optional topcoat layer can be applied over at least a portion of the reservoir layer and to serve as a rate limiting membrane which helps to control the rate of release of the drug. The topcoat layer can be essentially free from any active agents or drugs.

In one embodiment, any or all of the layers of the stent coating, can be made of a polymer that is both biologically beneficial and biologically degradable, erodable, absorbable, and/or resorbable. In another embodiment, just the outermost layer of the coating can be limited to such a polymer.

To illustrate in more detail, in the stent coating having all three layers described above (i.e., the primer, the reservoir layer, and the topcoat layer), the outermost layer is the topcoat layer, which is made of a biologically absorbable block copolymer. In this case, optionally, the remaining layers (i.e., the primer and the reservoir layer) can be also fabricated of a biologically absorbable block copolymer; the block copolymer can be the same or different in each layer. If the topcoat layer is not used, the stent coating can have only two layers: the optional primer and the reservoir. The reservoir in this case is the outermost layer of the stent coating and is made of a biologically absorbable block copolymer. Optionally, the primer can be also fabricated of a biologically absorbable block copolymer, which can be the same or different in the reservoir and in the primer. In one embodiment, the biologically absorbable copolymers that can be used for making any of the stent coating layers include poly(ester amides) (PEA). Optionally, in some other embodiments, condensation copolymers, such as poly(esters) having no amide bonds, can be used instead of PEAs.

The synthetic techniques that can be used for obtaining both the PEAs and the poly(esters) are described below in the application. Generally, the PEAs are products of reaction between at least one reagent from group A, at least one reagent from group B and a reagent $C_1$ from group C. The poly(esters) are products of reaction between at least one reagent from group A and a reagent $C_2$ from group C. The precursor-reagents from groups A, B, and C that can be used are characterized as follows.

A. Group A Reagents.

The group A precursor-reagents (hereinafter, "reagents") that can be used for synthesizing the biologically absorbable copolymers according to embodiments of the present invention are summarized in Table 1. The definition used to describe a chemical family to which each of the group A reagents belongs is also provided in Table 1.

TABLE 1

| | | Group A Reagents | |
|---|---|---|---|
| No. | Code | Reagent General Formula | Reagent Definition |
| 1 | $A_1$ | $H_2N-\underset{R_1}{\underset{|}{CH}}-\underset{}{\overset{O}{\overset{\|}{C}}}-O-X-O-\overset{O}{\overset{\|}{C}}-\underset{R_1}{\underset{|}{CH}}-NH_2$ | Diol-diamine |

TABLE 1-continued

Group A Reagents

| No. | Code | Reagent General Formula | Reagent Definition |
|---|---|---|---|
| 2 | $A_2$ | HO—$R_2$—C(=O)—NH—Y—NH—C(=O)—$R_2$—OH | Amidediol |
| 3 | $A_3$ | HO—X—OH | Diol |
| 4 | $A_4$ | $H_2N$—Y—$NH_2$ | Diamine |

In the general formulae of compounds $A_1$, $A_2$, $A_3$, and $A_4$ presented in Table 1, the substitutents $R_1$, $R_2$, X, and Y can be as follows:

$R_1$—(a) hydrogen;
  (b) methyl (—$CH_3$);
  (c) iso-propyl (-i-$C_3H_7$);
  (d) sec-butyl (-sec-$C_4H_9$);
  (e) iso-butyl (-i-$C_4H_9$); or
  (f) benzyl (—$C_6H_5$);

$R_2$—(a) methylene (—$CH_2$—);
  (b) ethylene (—$CH_2CH_2$—);
  (c) methylmethylene [—$CH(CH_3)$—];
  (d) straight chained or branched propylene, such as:
    (d1) n-propylene (—$CH_2CH_2CH_2$—);
    (d2) iso-propylene [—$CH_2CH(CH_3)$—]; or
    (d3) ethylmethylene [—$CH(CH_2CH_3)$—];
  (e) straight chained or branched butylene, such as:
    (e1) n-butylene (—$CH_2CH_2CH_2CH_2$—),
    (e2) iso-butylene [—$CH_2CH(CH_3)CH_2$—], or
    (e3) sec-butylene [—$CH(CH_2CH_3)CH_2$—];
  (f) straight chained or branched pentylene, such as:
    (f1) n-pentylene (—$CH_2CH_2CH_2CH_2CH_2$—),
    (f2) iso-pentylene [—$C(CH_3)_2CH_2CH_2$—],
    (f3) neopentylene {—$CH[C(CH_3)_3]$—},
    (f4) 2-methyl-1-butylene [—$C(CH_3)(CH_2CH_3)CH_2$—],
    (f5) sec-iso-pentylene [—$C(CH_3)_2CH(CH_3)$—], or
    (f6) methylpropylmethylene [—$C(CH_3)(CH_2CH_2CH_3)$—]; or
  (g) groups that are present in some amino acids, such as:
    (g1) methyleneamide (present in asparagine) [—$CH_2(CONH_2)$—];
    (g2) ethyleneamide (present in glutamine) [—$CH_2CH_2(CONH_2)$—];
    (g3) methylmercaptomethylmethylene (present in methionine) [—$CH_2(CH_2SCH_3)$—]; or
    (g4) n-propyleneamino group (—$CH_2CH_2CH_2NH$—) which is derived from 2-pyrrolidine group present (present in proline);

X—straight chained or branched aliphatic alkylene group $C_nH_{2n}$, wherein n is an integer between 2 and 16, e.g., methylene, ethylene, propylene, butylene, amylene (pentylene), hexylene, heptylene, octylene, nonylene, decylene, undecylene, or dodecylene group; and Y—straight chained or branched aliphatic alkylene group $C_2H_4$ (ethylene), $C_3H_6$ (propylene), $C_4H_8$ (butylene), or $C_5H_{10}$ (pentylene also known as amylene).

The reagent $A_1$ is a diol-diamine that can be synthesized by condensation of two molar equivalents of an amino acid and one molar equivalent of a diol. The synthesis can be carried under the conditions favoring esterification of the amino acid via the amino acid's carboxyl group. The reaction can be conducted under dehydrating conditions which include anhydrous environment and an elevated temperature, for example, about 50° C., and can be catalyzed by a strong acid or base, e.g., p-toluenesulfonic acid.

The diol that can be used to make the reagent Al has the formula HO—X—OH, where X is as defined above. Representative examples of diols that can be used include ethylene glycol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, and 1,12-dodecanediol. The amino acid that can be used to make the reagent $A_1$ has the formula $H_2N$—$CHR_1$—COOH, where $R_1$ is as defined above. Some amino acids that can be used are summarized in Table 2.

TABLE 2

Amino Acids That Can Be Used for Making the Reagent $A_1$

| | | Amino Acid ($H_2N$—$CHR_1$—COOH) | |
|---|---|---|---|
| No. | $R_1$ | Formula | Name |
| 1 | —H | $H_2N$—$CH_2$—COOH | glycine |
| 2 | —$CH_3$ | $H_2N$—CH($CH_3$)—COOH | alanine |
| 3 | —i-$C_3H_7$ | $H_2N$—CH(CH($CH_3$)$_2$)—COOH | valine |
| 4 | —sec—$C_4H_9$ | $H_2N$—CH(CH($CH_3$)$CH_2CH_3$)—COOH | isoleucine |

TABLE 2-continued

Amino Acids That Can Be Used for Making the Reagent $A_1$

Amino Acid ($H_2N$—$CHR_1$—COOH)

| No. | $R_1$ | Formula | Name |
|---|---|---|---|
| 5 | —i-$C_4H_9$ | $CH_3$—CH($CH_3$)—$CH_2$—CH($H_2N$)—COOH | leucine |
| 6 | $C_6H_5CH_2$— | $C_6H_5$—$CH_2$—CH($H_2N$)—COOH | phenyl alanine |
| 7 | —$(CH_2)_2$—S—$CH_3$ | $CH_2$—$CH_2$—S—$CH_3$ on CH($H_2N$)—COOH | methionine (α-amino-γ-methylmercaptobutyric acid) |
| 8 | —$CH_2$—C(O)—$NH_2$ | $CH_2$—C(O)—$NH_2$ on CH($H_2N$)—COOH | asparagine (α-amino-succinamic acid) |
| 9 | —$(CH_2)_2$—C(O)—$NH_2$ | $CH_2$—$CH_2$—C(O)—$NH_2$ on CH($H_2N$)—COOH | glutamine (2-amino-glutaramic acid) |

In addition to amino acids listed in Table 2, alternatively other amino acids can be used. One example of such alternative amino acids is proline (2-pyrrolidine carboxylic acid). Other alternative amino acids that can be used include some amino acids having free hydroxyl groups or second carboxyl groups if the free hydroxyl groups or the second carboxyl groups are protected first. The protection is needed so as to avoid interference when reagent $A_1$ is subsequently reacted with reagents of groups B and C, as discussed above. Examples of the amino acids that can be used after the free hydroxyl or second carboxyl groups are protected include tyrosine, serine, or glutamic acid.

The reagent $A_2$ is an amidediol that can be synthesized by condensation of two molar equivalents of a hydroxy acid and one molar equivalent of a diamine. The synthesis can be carried under the conditions favoring formation of an amide bond. The reaction can be conducted under dehydrating conditions, which include anhydrous environment and can be catalyzed by a strong base. Simple heating of the neat starting materials with the simultaneous removal of generated water by distillation can also be used.

The diamine that can be used to make the reagent $A_2$ has the formula $H_2N$—Y—$NH_2$, where Y is as defined above. Accordingly, examples of diamines that can be used include 1,4-butanediamine (putrescine) (Y=$CH_2CH_2CH_2CH_2$). Alternatively, other diamines, such as 1,2-ethanediamine (Y=$CH_2CH_2$) or 1,5-pentanediamine (cadavarene) (Y=$CH_2CH_2CH_2CH_2CH_2$) can be used. The hydroxy acid that can be used to make the reagent $A_2$ has the formula HO—$R_2$—COOH, where $R_2$ is as defined above. Some hydroxy acids that can be used are summarized in Table 3.

TABLE 3

Hydroxy Acids That Can Be Used For Making The Reagent $A_2$

Hydroxy Acid (HO—$R_2$—COOH)

| No. | $R_2$ | Formula | Name |
|---|---|---|---|
| 1 | —$CH_2$— | HO—$CH_2$—COOH | glycolic (hydroxyacetic acid) |
| 2 | —$CH_2$—$CH_2$— | HO—$CH_2$—$CH_2$—COOH | β-hydroxypropionic acid |
| 3 | —CH($CH_3$)— | HO—CH($CH_3$)—COOH | lactic (α-hydroxypropionic) acid |
| 4 | —CH($CH_3$)—$CH_2$— | HO—CH($CH_3$)—$CH_2$—COOH | β-hydroxybutyric acid |
| 5 | —CH($CH_2CH_2CH_3$)— | $CH_3$—$CH_2$—$CH_2$—CH(HO)—COOH | α-hydroxyvaleric acid |
| 6 | —CH($CH_2CH_3$)—$CH_2$— | $CH_3$—$CH_2$—CH(HO)—$CH_2$—COOH | β-hydroxyvaleric acid |
| 7 | —$(CH_2)_5$— | HO—$(CH_2)_5$—COOH | ε-hydroxycaproic acid |

TABLE 3-continued

Hydroxy Acids That Can Be Used For Making The Reagent $A_2$

Hydroxy Acid (HO—$R_2$—COOH)

| No. | $R_2$ | Formula | Name |
|---|---|---|---|
| 8 | —CH— <br> \| <br> $CH_3$—$(CH_2)_2$—$CH_2$ | $CH_3$—$(CH_2)_3$—CH—COOH <br> \| <br> OH | α-hydroxycaproic acid |
| 8 | —CH—$CH_2$— <br> \| <br> $CH_3$—$CH_2$—$CH_2$ | $CH_3$—$(CH_2)_2$—CH—$CH_2$—COOH <br> \| <br> OH | α-hydroxycaproic acid |
| 9 | —$(CH_2)_2$—CH— <br> \| <br> $CH_3$—$CH_2$ | $CH_3$—$CH_2$—CH—$(CH_2)_2$—COOH <br> \| <br> OH | δ-hydroxycaproic acid |

The reagent $A_3$ is a common simple diol having the formula HO—X—OH, where X is as defined above; and the reagent $A_4$ is a common simple diamine having the formula $H_2N$—Y—$NH_2$, where Y is as defined above.

B. Group B Reagents.

The group B reagents that can be used for synthesizing the biologically absorbable copolymers according to embodiments of the present invention are summarized in Table 4. Exemplary definitions used to describe a chemical family to which each of the group B reagents belongs is also provided in Table 4.

TABLE 4

Group B Reagents

| No. | Code | Reagent General Formula | Exemplary Reagent Definition ($R_4$ = PEG) |
|---|---|---|---|
| 1 | $B_1$ | $H_2N$—CH($R_1$)—C(=O)—O—$R_4$—O—C(=O)—CH($R_1$)—$NH_2$ | PEG-diester-diamine |
| 2 | $B_2$ | HO—$R_2$—C(=O)—NH—$R_4$—NH—C(=O)—$R_2$—OH | PEG-amidediol |
| 3 | $B_3$ | HO—$R_4$—OH | PEG-diol |
| 4 | $B_4$ | $H_2N$—$R_4$—$NH_2$ | PEG-diamine |

In general formulae of compounds $B_1$, $B_2$, $B_3$, and $B_4$ presented in Table 4, the substituents $R_1$ and $R_2$ are as defined above. One example of the $R_4$ moiety that can be used is a moiety derived from poly(ethylene glycol) (PEG). Alternatively, other biologically beneficial moieties can be used as $R_4$, for example, moieties derived from poly(propylene glycol) (PPG), random or block copolymers of PEG and PPG, hyaluronic acid, poly(2-hydroxyethylmethacrylate), poly(3-hydroxypropylmethacrylamide), or cellulosics.

The reagent $B_1$ can be a PEG-diester-diamine moiety (i.e., when $R_4$=PEG) that can be synthesized by condensation of two molar equivalents of an amino acid and one molar equivalent of PEG. The synthesis can be carried under the conditions favoring esterification of the amino acid via the carboxyl group. The reaction can be conducted under dehydrating conditions which include anhydrous environment and an elevated temperature, for example, about 50° C., and can be catalyzed by a strong acid or base, e.g., p-toluenesulfonic acid. To make the reagent $B_1$, PEG having molecular weight between about 100 and 4,000 Daltons, for example, about 300 Daltons, can be used. Any amino acid listed in Table 2 can be used. Alternatively, other amino acids can be used, for example, tyrosine, serine, or glutamic acid, if free hydroxyl groups of tyrosine and serine or the second carboxyl group of glutamic acid are protected so as not to interfere when reagent $B_1$ is subsequently reacted with reagents of groups A and C, as discussed above.

The reagent $B_2$ can be a PEG-amidediol that can be synthesized by condensation of two molar equivalents of a hydroxy acid and one molar equivalent of a PEG-diamine. The synthesis can be carried under the conditions favoring formation of an amide bond. The reaction can be conducted under dehydrating conditions which include anhydrous environment, and can be catalyzed by a strong base, or prepared from neat reagents by heating at high temperature with the simultaneous removal of generated water, e.g., the removal of water by distillation. Any hydroxy acid listed in Table 3 can be used. PEG terminated with amino groups on both ends (PEG-diamine reagent $B_4$) can be obtained from Huntsman Chemical Co. of Houston, Tex. under the trade name JEFFAMINE.

C. Group C Reagents.

The group C reagents that can be used for synthesizing the biologically absorbable copolymers according to embodiments of the present invention are summarized in Table 5. The definition used to describe a chemical family to which each of the group C reagents belongs is also provided in Table 5.

TABLE 5

Group C Reagents

| No. | Code | Reagent General Formula | Reagent Definition |
|-----|------|-------------------------|---------------------|
| 1 | $C_1$ | HO—C(=O)—$R_3$—C(=O)—OH | Dicarboxylic acid |
| 2 | $C_2$ | HO—C(=O)—PEG—C(=O)—OH | PEG-dicarboxylic acid |

In general formula of compound C, presented in Table 5, the substituent $R_3$ is simply a covalent bond, or a straight chained or branched aliphatic alkylene group $C_nH_{2n}$, wherein n is an integer having a value between 0 and 12, e.g. a single bond (n=0), methylene, ethylene, propylene, butylene, amylene (pentylene), hexylene, heptylene, octylene, nonylene, decylene, undecylene, or dodecylene group, or an aromatic group, e.g., phenyl or para-phenylene. Some examples of dicarboxylic acids that can be used as the reagent $C_1$ are summarized in Table 6.

TABLE 6

Dicarboxylic Acids That Can Be Used As The Reagent $C_1$

Dicarboxylic Acid (HOOC—$R_3$—COOH)

| No. | $R_3$ | Formula | Name |
|-----|-------|---------|------|
| 1 | —$(CH_2)_2$— | HOOC—$(CH_2)_2$—COOH | succinic (butanedioic) acid |
| 2 | —$(CH_2)_4$— | HOOC—$(CH_2)_4$—COOH | adipic (hexanedioic) acid |
| 3 | —$(CH_2)_8$— | HOOC—$(CH_2)_8$—COOH | sebacic (decanedioic) acid |
| 4 | (p)—$C_6H_4$— | HOOC—$(p)C_6H_4$—COOH | terephthalic (1,4-benzene dicarboxylic) acid |

In addition to the dicarboxylic acids listed in Table 6, examples of other dicarboxylic acids that can be also used include oxalic acid, malonic acid, glutaric acid, pimelic acid, suberic acid, or azelaic acid. As mentioned above, to synthesize the PEAs, at least one reagent of group A can be reacted with at least one reagent of group B and reagent $C_1$. To make the poly(esters), at least one reagent of group A can be reacted with reagent $C_2$.

One of several routes can be utilized to synthesize the polymers of this invention. Those having ordinary skill in the art can appreciate that the reagents of groups A, B, and C may themselves contain hydrolysable bonds, i.e. ester or amide bonds. These reagents can be then polymerized, the polymerization creating additional bonds that may be both ester and amide bonds, only amide bonds, or only ester bonds. Given that the reagents can be obtained separately, the types of polymers formed during the polymerization can belong to one of the following four categories (A), (B), (C), or (D):

(A) Polymers in which amide bonds are formed between reagents which themselves contain ester bonds. Using the reagent codes defined earlier, these polymers can be described as products of reaction between:
  (1) $A_1$, $B_1$ and $C_1$ ($A_1$-$B_1$-$C_1$);
  (2) $A_1$, $B_4$ and $C_1$ ($A_1$-$B_4$-$C_1$);
  (3) $A_4$, $B_1$ and $C_1$ ($A_4$-$B_1$-$C_1$); and
  (4) $A_1$ and $C_2$ ($A_1$-$C_2$).

(B) Polymers in which amide bonds are formed between reagents which themselves contain neither ester nor amide bonds. Using the reagent codes defined earlier, these polymers can be described as products of reaction between:
  (1) $A_4$, $B_4$ and $C_1$ ($A_4$-$B_4$-$C_1$); and
  (2) $A_4$ and $C_2$ ($A_4$-$C_2$).

(C) Polymers in which both ester and amide bonds are formed between the reagents. The subunits themselves may contain ester and amide bonds, only ester bonds, only amide bonds, or neither ester nor amide bonds. Using the reagent codes defined earlier, these polymers can be described as products of reaction between:
  (1) $A_1$, $B_2$ and $C_1$ ($A_1$-$B_2$-$C_1$);
  (2) $A_1$, $B_3$ and $C_1$ ($A_1$-$B_3$-$C_1$);
  (3) $A_2$, $B_1$ and $C_1$ ($A_2$-$B_1$-$C_1$);
  (4) $A_2$, $B_4$ and $C_1$ ($A_2$-$B_4$-$C_1$);
  (5) $A_3$, $B_1$ and $C_1$ ($A_3$-$B_1$-$C_1$);
  (6) $A_3$, $B_4$ and $C_1$ ($A_3$-$B_4$-$C_1$);
  (7) $A_4$, $B_2$ and $C_1$ ($A_4$-$B_2$-$C_1$); and
  (8) $A_4$, $B_3$ and $C_1$ ($A_4$-$B_3$-$C_1$).

(D) Polymers in which ester bonds are formed between reagents which themselves may contain amide bonds, or neither amide nor ester bonds. Using the reagent codes defined earlier, these polymers can be described as products of reaction between:
  (1) $A_2$, $B_2$ and $C_1$ ($A_2$-$B_2$-$C_1$);
  (2) $A_2$, $B_3$ and $C_1$ ($A_2$-$B_3$-$C_1$);
  (3) $A_2$ and $C_2$ ($A_2$-$C_2$);
  (4) $A_3$, $B_2$ and $C_1$ ($A_3$-$B_2$-$C_1$);
  (5) $A_3$, $B_3$ and $C_1$ ($A_3$-$B_3$-$C_1$); and
  (6) $A_3$ and $C_2$ ($A_3$-$C_2$).

Due to the types of bonds being formed, and the types of bonds present, those having ordinary skill in the art will understand that the polymerization scheme need be adjusted for each category in order to form the desired polymer while not hydrolyzing or degrading the existing bonds in the reagents, or creating uncontrolled, mixed species. Some examples of the synthesis of particular polymers are provided below in the "Examples" section of the present application.

As a result of the synthesis, biologically absorbable PEAs having a general formula (A) or poly(esters) having a general formula (B) can be obtained:

$$-[M\text{-}P]_m\text{-}[M\text{-}Q]_n\text{-} \qquad (A)$$

$$-[M_1\text{-}P]_p— \qquad (B)$$

wherein:

M is a moiety represented by the structure

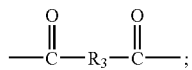

P is a moiety including

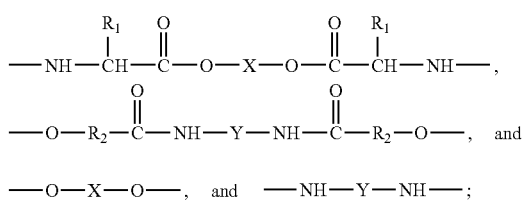

Q is a moiety selected from a group consisting of

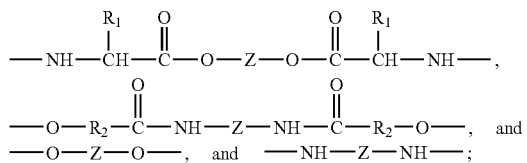

and $M_1$ is a moiety represented by the structure

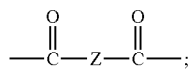

$R_1$, $R_2$, $R_3$, X and Y are substitutents and moieties as defined above;

Z is a moiety that can be derived from a compound selected from a group consisting of poly(ethylene glycol)(PEG), poly(propylene glycol) (PPG), random or block copolymers of PEG and PPG, hyaluronic acid, poly(2-hydroxyethylmethacrylate), poly(3-hydroxypropyl methacrylamide), poly(styrene sulfonate), poly(vinyl pyrrolidone), and cellulosics; and m, n, and p are integers where the value of m can be between 5 and 1,800, the value of n can be between 1 and 800 and the value of p can be between 4 and 1,500.

Any layer of the stent coating can contain any amount of the biologically absorbable copolymers described above, or a blend of more than one of such copolymers. If less than 100% of the layer is made of the biologically absorbable copolymers, or blends thereof, described above, alternative polymers can comprise the balance. Examples of the alternative polymers that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoropropene), poly(N-vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the stent coatings include N,N-dimethylacetamide (DMAC), N,N-dimethylformamide (DMF), tethrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);

(2) water, i-propanol, and DMAC (e.g., a 10:3:87 by mass mixture);

(3) i-propanol, and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. a 50:50 by mass mixture);

(6) acetone, FLUX REMOVER AMS, and xylene (e.g., a 10:50:40 by mass mixture); and (7) 1,1,2-trichloroethane and chloroform (e.g., a 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

The therapeutic substance which can be used in the reservoir layer can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The coatings and methods of the present invention have been described with reference to a stent, e.g., a balloon expandable or self-expandable stent. The use of the coating is not limited to stents, and the coating can also be used with a variety of other medical devices, such as implantable medical devices. Examples of the implantable medical device that can be used in conjunction with the embodiments of this invention include stent-grafts, grafts (e.g., aortic grafts), catheters, guidewires, artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Medical devices can be also made from the materials of the invention. Moreover, the polymers can be used for a variety of medical applications, including particles for drug delivery to embolize blood vessels. The polymers of the present invention can have a variety of medical applications, including the treatment of stenosis, restenosis, and cancer.

3. EXAMPLES

The following examples are provided to further illustrate embodiments of the present invention.

Example 1

A copolymer having formula (III) can be synthesized and used in practice of the invention.

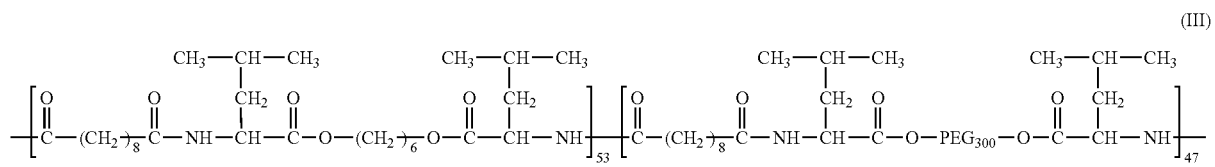

The copolymer (III) is a product of copolymerization of reagents $A_1$, $B_1$, and $C_1$. $A_1$ can be a diol-diamine shown in Table 1 where $R_1$ is $i$-$C_4H_9$ and X is $(CH_2)_6$. In other words, $A_1$ can be synthesized by condensation of leucine with 1,6-hexanediol. $B_1$ can be a PEG-diester-diamine shown in Table 4 where $R_1$ is $i$-$C_4H_9$ and $PEG_{300}$ symbolizes a moiety derived from poly(ethylene glycol) having molecular weight of about 300 Daltons. In other words, $B_1$ can be synthesized by condensation of leucine with poly(ethylene glycol) having molecular weight of about 300 Daltons. $C_1$ can be a dicarboxylic acid shown in Table 5 where $R_3$ is $(CH_2)8$ (sebacic acid, which is also shown in Table 6).

To synthesize copolymer (III), about 30.8 ml dry triethylamine (about 0.22 mole) in about 55 ml dry solvent N,N'-dimethylacetamide at room temperature can be added to a mixture of:

(a) about 36.37 g (about 0.053 mole) di-para-toluenesulfonic acid salt of bis-(L-leucine)-1,6-hexylene diester;

(b) about 39.3 g (about 0.047 mole) di-para-toluenesulphonic acid salt of bis-(L-leucine)-PEG300 diester; and (c) about 44.4 g (about 0.1 mole) di-para-nitrophenyl sebacinate.

The mixture can be stirred until full dissolution and then the temperature can be raised to about 80° C. After stirring for about 24 hours, the viscous mixture can be cooled to room temperature, diluted with about 100 ml ethanol, and precipitated into an excess of water. The separated polymer can be thoroughly washed with water, spread thinly onto a TEFLON pan, and dried at room temperature under vacuum (about 70 mm Hg) for about 24 hours.

Example 2

A copolymer having formula (IV) can be synthesized and used in practice of the invention.

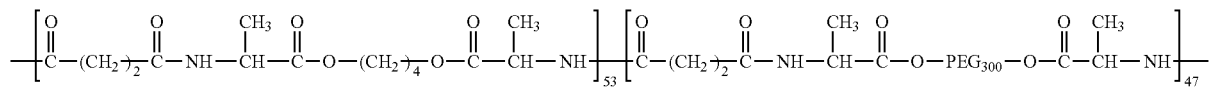

(IV)

The copolymer (IV) is a product of copolymerization of reagents $A_1$, $B_1$, and $C_1$. $A_1$ can be a diol-diamine shown in Table 1, where $R_1$ is $CH_3$ and X is $(CH_2)_4$. In other words, $A_1$ can be synthesized by condensation of alanine with 1,4-butanediol. $B_1$ can be a PEG-diester-diamine shown in Table 4 where $R_1$ is i-$C_4H_9$ and $PEG_{300}$ symbolizes a moiety derived from poly(ethylene glycol) having molecular weight of about 300 Daltons. In other words, $B_1$ can be synthesized by condensation of alanine with poly(ethylene glycol) having molecular weight of about 300 Daltons. $C_1$ can be a dicarboxylic acid shown in Table 5 where $R_3$ is $(CH_2)_2$ (succinic acid, which is also shown in Table 6).

To synthesize copolymer (IV), about 30.8 ml dry triethylamine (about 0.22 mole), in about 55 ml dry solvent N,N'-dimethylacetamide, at room temperature, can be added to a mixture of:

(a) about 30.43 g (about 0.053 mole) di-para-toluenesulfonic acid salt of bis-(L-alanine)-1,4-butylene diester;

(b) about 36.86 g (about 0.047 mole) di-para-toluenesulfonic acid salt of bis-(L-alanine)-PEG300 diester; and (c) about 36.0 g (about 0.1 mole) di-para-nitrophenyl succinate.

The mixture can be stirred until full dissolution and then the temperature can be raised to about 80° C. After stirring for about 24 hours, the viscous mixture can be cooled to room temperature, diluted with about 100 ml ethanol, and precipitated into an excess of water. The separated polymer is thoroughly washed with water, spread thinly into a TEFLON pan, and dried at room temperature under vacuum (about 70 mm Hg) for about 24 hours.

Example 3

A copolymer having formula (V) can be synthesized and used in practice of the invention.

The copolymer (V) is a product of copolymerization of reagents $A_1$, $B_1$, and $C_1$. $A_1$ can be a diol-diamine shown in Table 1 where $R_1$ is i-$C_4H_9$ and X is $(CH_2)_4$. In other words, $A_1$ can be synthesized by condensation of leucine with 1,4-butanediol. $B_1$ can be a PEG-diester-diamine shown in Table 4 where $R_1$ is i-$C_4H_9$ and $PEG_{300}$ symbolizes a moiety derived from poly(ethylene glycol) having molecular weight of about 300 Daltons. In other words, $B_1$ can be synthesized by condensation of leucine with poly(ethylene glycol) having molecular weight of about 300 Daltons. $C_1$ can be a dicarboxylic acid shown in Table 5 where $R_3$ is para-$C_6H_4$ (terephthalic acid, which is also shown in Table 6).

The copolymer (V) can be obtained using the same synthetic technique as described in Example 2 for copolymer (IV), except di-para-nitrophenyl terephthalate can be used to make the copolymer (V), instead of di-para-nitrophenyl succinate. In copolymer (V), the value of n can be between about 64 and about 97 and the value of m can be between about 3 and about 36, where m+n=100.

Example 4

A copolymer having formula (VI) can be synthesized and used in practice of the invention.

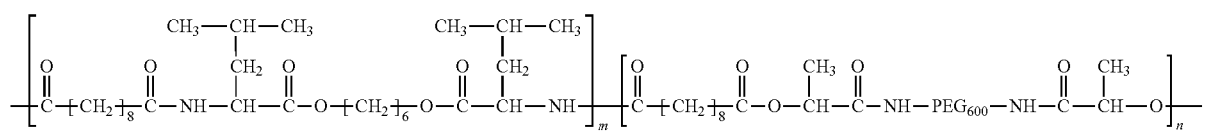

(VI)

The copolymer (VI) is a product of copolymerization of reagents $A_1$, $B_2$, and $C_1$. $A_1$ can be a diol-diamine shown in Table 1 where $R_1$ is i-$C_4H_9$ and X is $(CH_2)_6$. In other words, $A_1$ can be synthesized by condensation of leucine with 1,6-hexanediol. $B_2$ can be a PEG-amidediol shown in Table 4 where $R_2$ is methylmethylene $CH(CH_3)$.

In other words, $B_2$ can be synthesized by condensation of lactic acid with PEG-diamine shown as reagent $B_4$ in Table 4. PEG-diamine can be based on poly(ethylene glycol) having molecular weight of about 600 Daltons, which is symbolized by the abbreviation $PEG_{600}$.

For example, JEFFAMINE ED-600 available from Huntsman Corp. can be used. JEFFAMINE ED-600 is a trade name of O,O'-bis-[(2-aminopropyl) poly(propylene glycol)-block-poly(ethylene glycol)-block-poly(propylene glycol)], which

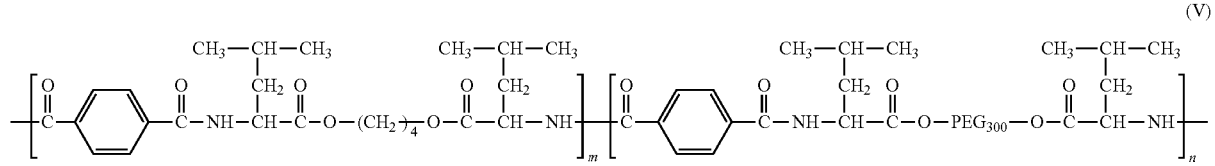

(V)

is a polyether diamine with a polyalkylene oxide backbone. The molecular weight of JEFFAMINE ED-600 is about 600 Daltons.

$C_1$ can be a dicarboxylic acid shown in Table 5 where $R_3$ is $(CH_2)_8$ (sebacic acid, which is also shown in Table 6). In copolymer (VI), the value of n can be between about 60 and about 93 and the value of m can be between about 7 and about 40, where m+n=100.

Example 5

A copolymer having formula (VII) can be synthesized and used in practice of the invention.

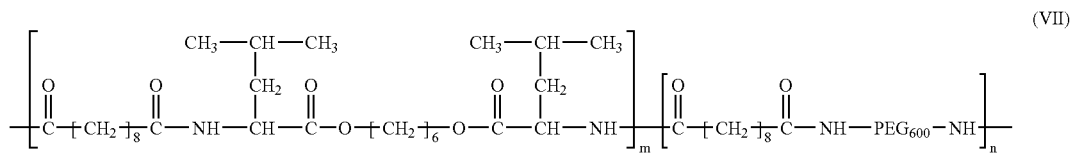

(VII)

The copolymer (VII) can be synthesized in same way as the copolymer (VI) of Example 4, except instead of a reagent $B_2$ (e.g., PEG-amidediol), reagent $B_4$ (e.g., PEG-diamine) shown in Table 4 can be used. In copolymer (VII), the value of n can be between about 59 and about 96 and the value of m can be between about 4 and about 41, where m+n=100.

Example 6

A copolymer having formula (VIII) can be synthesized and used in practice of the invention.

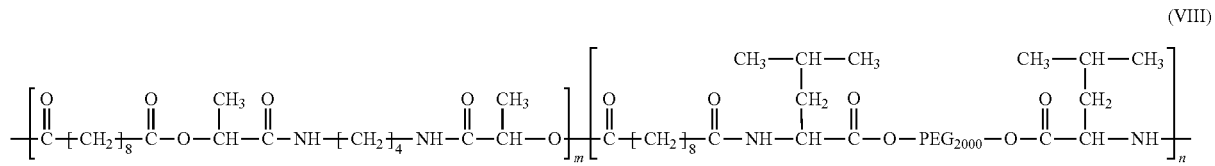

(VIII)

The copolymer (VIII) is a product of copolymerization of reagents $A_2$, $B_1$, and $C_1$. $A_2$ can be an amidediol shown in Table 1 where $R_2$ is methylmethylene $CH(CH_3)$ and Y is $(CH_2)_4$. In other words, $A_2$ can be synthesized by condensation of lactic acid with the 1,4-diamino butane (putrescine).

$B_1$ can be a PEG-diester-diamine shown in Table 4 where $R_1$ is i-$C_4H_9$. In other words, $B_1$ can be synthesized by condensation of leucine with poly(ethylene glycol) having molecular weight of about 2,000 Daltons, which is symbolized by the abbreviation $PEG_{2000}$.

$C_1$ can be a dicarboxylic acid shown in Table 5 where $R_3$ is $(CH_2)_8$ (sebacic acid, which is also shown in Table 6). In copolymer (VIII), the value of n can be between about 86 and about 99 and the value of m can be between about 1 and about 14, where m+n=100.

Example 7

A copolymer having formula (IX) can be synthesized and used in practice of the invention.

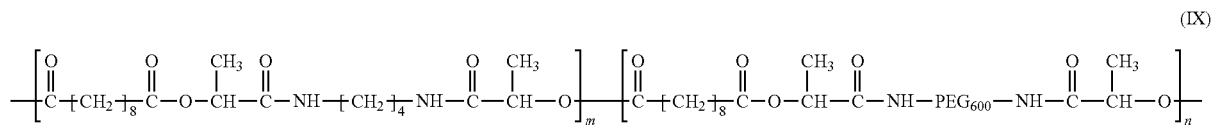

(IX)

The copolymer (IX) can be synthesized in same way as the copolymer (VIII) of Example 6, except instead of a reagent $B_1$ (PEG-diester-diamine), reagent $B_2$ (PEG-amidediol) shown in Table 4 can be used, where $R_2$ is methylmethylene $CH(CH_3)$. In other words, $B_2$ can be synthesized by condensation of lactic acid with PEG-diamine shown as reagent $B_4$ in Table 4. PEG-diamine can be based on poly(ethylene glycol) having molecular weight of about 600 Daltons, which is symbolized by the abbreviation $PEG_{600}$. In copolymer (IX), the integer value of n can be between about 69 and about 98 and the value of m can be between about 2 and about 31, where m+n=100.

Example 8

A copolymer having formula (X) can be synthesized and used in practice of the invention.

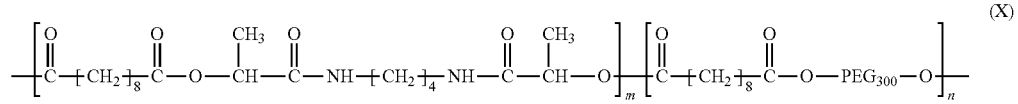

The copolymer (X) can be synthesized in same way as the copolymer (IX) of Example 7, except that a reagent $B_3$ shown in Table 4, $(HO-R_4-OH)$, for example, PEG-diol, can be used instead of a reagent $B_2$ (e.g., PEG-amidediol). PEG-diol can be based on poly(ethylene glycol) having molecular weight of about 300 Daltons, which is symbolized by the abbreviation $PEG_{300}$.

$A_2$ and $B_3$ reagents can be combined and reacted first to form an $A_2$-$B_3$ moiety, followed by adding a $C_1$ reagent and completing polycondensation. The conditions for the synthesis can be determined by those having ordinary skill in the art. For example, the final step of the reaction (reacting $C_1$ with the $A_2$-$B_3$ moiety) can be conducted in the presence of a coupling agent such as carbodiimide.

Optionally, instead of a $C_1$ diacid, a dichloride of the diacid can be used, for instance, sebacyl dichloride. In copolymer (X), the value of n can be between about 54 and about 96 and the value of m can be between about 4 and about 46, where m+n=100.

Alternative versions of the copolymer (X) can be also synthesized to make the copolymer (X) harder. For example, an amino acid with shorter $R_2$ group or a shorter chain diamine (e.g., ethanediamine instead of 1,4-butanediamine) can be used for preparing the reagent $A_2$.

Other possible methods of increasing the hardness of the copolymer (X) include using a shorter dicarboxylic acid $C_1$ (e.g., adipic acid instead of sebacic acid), or using PEG with lower molecular weight, or reducing the proportion of the PEG-containing units in the overall copolymer (X).

Example 9

A copolymer having formula (XI) can be synthesized and used in practice of the invention.

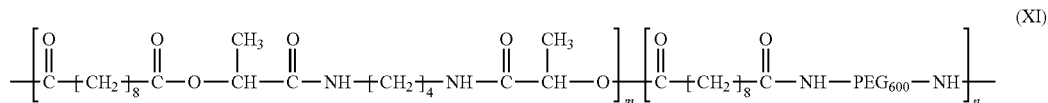

The copolymer (XI) can be synthesized in same way as the copolymer (X) of Example 9, except that a reagent $B_4$ (such as PEG-diamine) shown in Table 4 can be used instead of a reagent $B_3$ (e.g., PEG-diol). PEG-diamine can be based on poly(ethylene glycol) having molecular weight of about 600 Daltons, which is symbolized by the abbreviation $PEG_{600}$. In copolymer (XI), the value of n can be between about 3 and about 35, and the value of m can be between about 97 and about 65, where m+n=100.

Example 10

A copolymer having formula (XII) can be synthesized and used in practice of the invention.

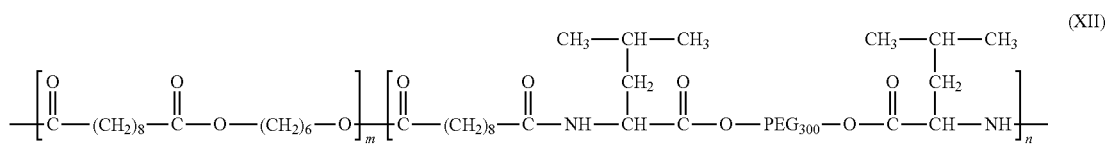

The copolymer (XII) can be synthesized in same way as the copolymer (VIII) of Example 6, except that a reagent $A_3$ (diol) shown in Table 1 can be used instead of a reagent $A_2$ (amidediol), where X is $(CH_2)_6$. In other words, 1,6-hexanediol can be used as the reagent $A_3$. A poly(ethylene glycol) moiety having molecular weight of about 300 Daltons can comprise a part of copolymer (XII), which is symbolized by the abbreviation $PEG_{300}$. In copolymer (XII), the value of n can be between about 98 and about 71 and the value of m can be between about 2 and about 29, where m+n=100.

Example 11

A copolymer having formula (XIII) can be synthesized and used in practice of the invention.

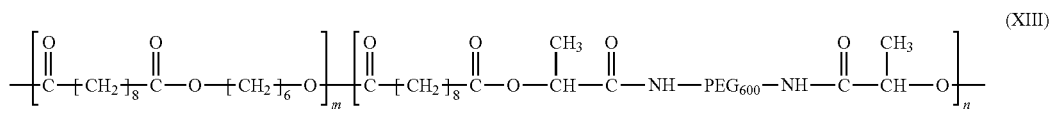

The copolymer (XIII) can be synthesized in same way as the copolymer (XII) of Example 10, except that a reagent $B_2$ (e.g., PEG-amidediol) shown in Table 4 can be used instead of a reagent $B_1$ (such as PEG-diester-diamine), where $R_2$ is methylmethylene $CH(CH_3)$. In other words, $B_2$ can be synthesized by condensation of lactic acid with PEG-diamine shown as reagent $B_4$ in Table 4. PEG-diamine can be based on poly(ethylene glycol) having molecular weight of about 600 Daltons, which is symbolized by the abbreviation $PEG_{600}$.

In copolymer (XIII), the value of n can be between about 98 and about 76 and the value of m can be between about 2 and about 24, where m+n=100.

Example 12

A copolymer having formula (XIV) can be synthesized and used in practice of the invention.

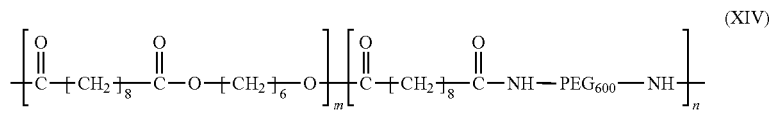

The copolymer (XIV) can be synthesized in same way as the copolymer (XIII) of Example 11, except that a reagent $B_4$ (e.g., PEG-diamine) as shown in Table 4 can be used instead of a reagent $B_2$ (such as PEG-amidediol). PEG-diamine can be based on poly(ethylene glycol) having molecular weight between about 300 and about 2,400 Daltons, for example, about 600 Daltons, which is symbolized by the abbreviation $PEG_{600}$. Reagent $A_3$ (1,6-hexanediol) and reagent $C_1$ (sebacic acid) can be combined and reacted first to form an $A_3$-$C_1$ moiety, followed by adding reagent $B_4$ and completing polycondensation. To facilitate the formation of the $A_3$-$C_1$ moiety, sebacyl dichloride can be used as the $C_1$ reagent instead of sebacic acid. The conditions for the synthesis can be determined by those having ordinary skill in the art.

In copolymer (XIV), the value of n can be between about 98 and about 73 and the value of m can be between about 2 and about 27, where m+n=100.

Example 13

A copolymer having formula (XV) can be synthesized and used in practice of the invention.

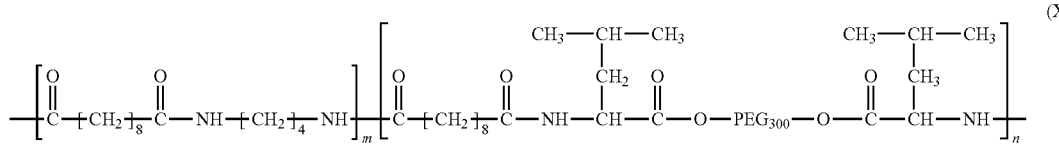
(XV)

The copolymer (XV) can be synthesized in same way as the copolymer (VIII) of Example 6, except that a reagent $A_4$ (diamine) shown in Table 1 can be used instead of a reagent $A_2$ (amidediol), where Y is $(CH_2)_4$.

In other words, putrescine can be used as the reagent $A_4$. A poly(ethylene glycol) moiety having molecular weight between about 300 Daltons and about 4,000 Daltons, for example, about 300 Daltons, can comprise a part of copolymer (XV), which is symbolized by the abbreviation $PEG_{300}$.

In copolymer (XV), the value of n can be between about 98 and about 73 and the value of m can be between about 2 and about 27, where m+n=100.

Example 14

A copolymer having formula (XVI) can be synthesized and used in practice of the invention.

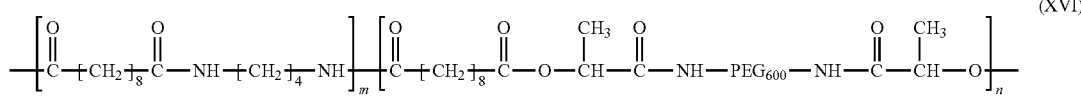
(XVI)

The copolymer (XVI) can be synthesized in same way as the copolymer (IX) of Example 7, except that a reagent $A_4$ (diamine) shown in Table 1 can be used instead of a reagent $A_2$ (amidediol), where Y is $(CH_2)_4$. In other words, putrescine can be used as the reagent $A_4$.

A poly(ethylene glycol) moiety having molecular weight between about 300 Daltons and about 4,000 Daltons, for example, about 600 Daltons, can comprise a part of copolymer (XVI), which is symbolized by the abbreviation $PEG_{600}$.

In copolymer (XVI), the value of n can be between about 98 and about 77, and the value of m can be between about 2 and about 23, where m+n=100.

Example 15

A copolymer having formula (XVII) can be synthesized and used in practice of the invention.

The copolymer (XVII) can be synthesized in same way as the copolymer (X) of Example 8, except that a reagent $A_4$ (diamine) shown in Table 1 can be used instead of a reagent $A_2$ (amidediol), where Y is $(CH_2)_4$. In other words, putrescine can be used as the reagent $A_4$.

A poly(ethylene glycol) moiety having molecular weight between about 300 Daltons and about 4,000 Daltons, for example, about 2,000 Daltons can comprise a part of copolymer (XVII), which is symbolized by the abbreviation $PEG_{2000}$.

In copolymer (XVII), the value of n can be between about 995 about 910 the value of m can be between about 5 and about 90, where m+n=1000.

Example 16

A copolymer having formula (XVIII) can be synthesized and used in practice of the invention.

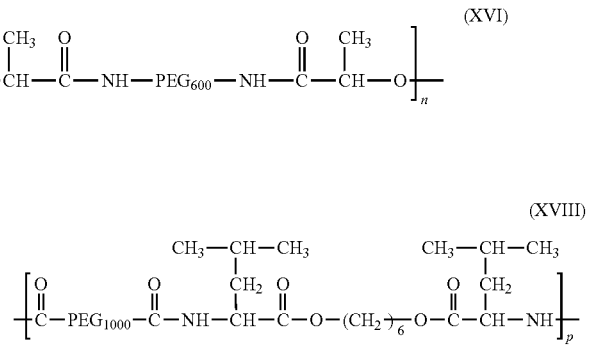
(XVIII)

To synthesize the copolymer (XVIII), reagents $A_1$ and $C_2$, can be combined in the molar ratio of about 1:1 and copolymerized. The conditions for the synthesis can be determined by those having ordinary skill in the art. $A_1$ can be a dioldiamine shown in Table 1, where $R_1$ is $i$-$C_4H_9$ and X is $(CH_2)_6$. In other words, $A_1$ can be synthesized by condensation of leucine with 1,6-hexanediol. $C_2$ can be a PEG-dicarboxylic acid shown in Table 5, derived from poly(ethylene glycol) having molecular weight of about 1,000 Daltons,

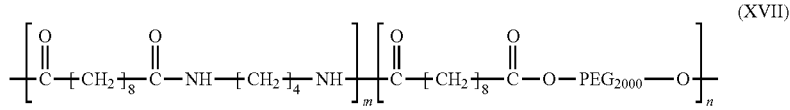
(XVII)

which is symbolized by the abbreviation $PEG_{1000}$. A total molecular weight of the copolymer (XVIII) can be between about 20,000 Daltons and about 50,000 Daltons. The value of the integer p can be between about 14 and about 360.

Example 17

A copolymer having formula (XIX) can be synthesized and used in practice of the invention.

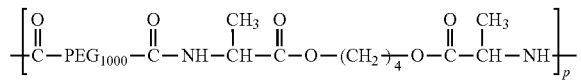

(XIX)

The copolymer (XIX) can be synthesized in same way as the copolymer (XVIII) of Example 16, except that a reagent $A_2$ (amidediol) shown in Table 1 can be used instead of a reagent $A_1$ (diol-diamine), where $R_2$ is methylmethylene $CH(CH_3)$, and Y is $(CH_2)_4$. In other words, $A_2$ can be synthesized by condensation of lactic acid with putrescine. $C_2$ can be a PEG-dicarboxylic acid shown in Table 5 derived from poly (ethylene glycol) having molecular weight of about 1,000 Daltons, which is symbolized by the abbreviation $PEG_{1000}$.

A total molecular weight of the copolymer (XIX) can be between about 20,000 Daltons and about 50,000 Daltons. The value of the integer p can be between about 15 and about 390.

Example 18

Co-poly-{[N,N'-adipoyl-bis-(L-alanine)-1,4-butylene diester]$_{37}$-[N,N'-adipoyl-bis-(L-alanine)-PEG300 diester]$_{67}$} having formula (XX) can be synthesized and used in practice of the invention. This copolymer belongs to category (A), type $A_1$-$B_1$—$C_1$, described above.

To synthesize the copolymer (XX), about 41 ml (about 0.293 mole) dry triethylamine in about 75 ml dry solvent N,N'-dimethylacetamide, at room temperature, can be added to a mixture of:

(a) about 28.64 g (about 0.0497 mole) di-para-toluene-sulfonic acid salt of bis-(L-alanine)-1,4-butylene diester;

(b) about 65.57 g (about 0.0834 mole) di-para-toluenesulphonic acid salt of bis-(L-alanine)-PEG300 diester; and (c) about 51.62 g (about 0.1331 mole) di-para-nitrophenyl adipate.

The mixture can be stirred until full dissolution and then the temperature can be raised to about 80° C. After stirring for about 24 hours, the viscous mixture can be cooled to room temperature, diluted with about 100 ml ethanol, and precipitated into an excess of water. The separated polymer can be thoroughly washed with water, spread thinly onto a TEFLON pan, and dried at room temperature under vacuum (about 70 mm Hg) for about 24 hours.

As amide bonds are formed in the presence of existing ester bonds, mild conditions need to be used, and this will be understood by those having ordinary skill in the art. For example, polymerization techniques using good leaving groups such as para-nitrophenol or carboxyl groups activated by carbodiimides can be used. In this invention, the range of stoichiometries can be determined by the desired mass content of PEG.

For example, the final polymer can contain between about 5 mass % and about 50 mass % of PEG. For copolymer (XX), this corresponds to molar ratios of the two blocks of (alanine/butanediol-adipic acid) ($A_1$-$C_1$ blocks) and (alanine/PEG-adipic acid) ($B_1$—$C_1$ blocks) between about 94:6 and about 12:88.

Example 19

Co-poly-{[N,N'-sebacyl-1,4-butylene diamide]$_{86}$-[N,N'-sebacyl-(ED-600)diamide]$_{14}$} having formula (XXI) can be synthesized and used in practice of the invention. This copolymer belongs to category (B), type ($A_4$-$B_4$—$C_1$), described above.

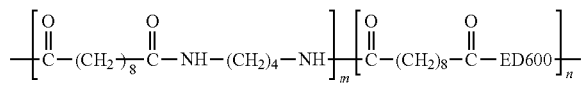

(XXI)

In formula (XXI), "ED-600" is an abbreviation symbolizing JEFFAMINE ED-600 polymer described above (see Example 4).

To synthesize the copolymer (XXI), about 104 ml (about 0.744 mole) dry triethylamine in about 65 ml dry solvent N,N'-dimethylacetamide, at room temperature, can be added to a mixture of:

(a) about 23.38 g (about 0.266 mole) dry 1,4-diaminobutane; and

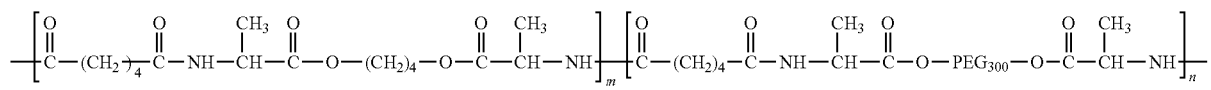

(XX)

(b) about 25 g (about 0.0417 mole) dry ED-600.

The mixture can be stirred, under a nitrogen atmosphere at room temperature, until full dissolution. The mixture can be cooled in ice water and about 80.75 g (about 0.338 mole) sebacoyl chloride can be added dropwise with stirring. The solution can be allowed to come to ambient temperature with stirring stirred continued overnight. The viscous mixture can then be precipitated into an excess of water. The separated polymer can be thoroughly washed with water, spread thinly into a TEFLON pan, and dried at room temperature under vacuum (about 70 mm Hg) for about 24 hours.

As only amide bonds are present, without any other hydrolysable groups, harsher synthetic conditions can be used for this category as understood by those having ordinary skill in the art. For example, acid chlorides can be used. The mass contents of PEG in the final copolymer (XXI) can be between about 5 mass % and about 50 mass %. For copolymer (XXI), this corresponds to molar ratios of the two blocks of diamine-sebacic acid ($A_4$-$C_1$ blocks) and ED-600-sebacic acid ($B_4$—$C_1$ blocks) of between about 97:3 and about 57:43.

Example 20

Co-poly-{[N,N'-succinyl-bis-(L-leucine)-1,3-propylene diester]$_{82}$-[succinyl-PEG$_{600}$ diester]$_{18}$} having formula (XXII) can be synthesized and used in practice of the invention. This copolymer belongs to category (C), type (A$_1$-B$_3$—C$_1$), described above.

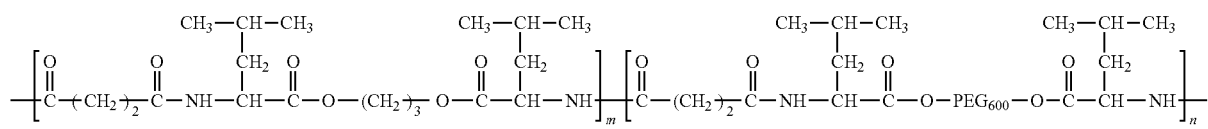

(XXII)

To synthesize the copolymer (XXII), about 26.8 g (about 0.227 mole) succinic acid, and about 52.3 g (about 0.454 mole) N-hydroxysuccinimide can be added to about 100 ml dry N,N'-dimethylformamide at room temperature under nitrogen and dissolved with stirring. About 93.67 g (about 0.454 mole) dicyclohexylcarbodiimide (DCC) can be to the mixture added, and the mixture can be allowed to stir for about 16 hours at room temperature.

The reaction mixture can be filtered through filter paper to remove the urea byproduct, and the solution can be placed into a reaction flask. The following compounds can then be added to the reaction mixture with continued stirring:

(a) about 55.9 g (about 0.185 mole) the free base of bis-(L-leucine)-1,3-propylene diester; and (b) about 25 g (about 0.0417 mole) poly(ethylene glycol) having molecular weight of about 600 Daltons (PEG600).

The mixture can be stirred at room temperature for about 2 hours and then the temperature can be increased to about 60° C. and stirred for about two more hours. The polymer can precipitated by adding the reaction solution dropwise to about 2 liters of ethyl acetate with stirring. The precipitated polymer can be placed as a thin layer into a TEFLON pan and dried at room temperature under vacuum (about 70 mm Hg) for about 24 hours.

In this category, both amide and ester bonds are present in the copolymer. Accordingly, mild conditions need to be used, as understood by those having ordinary skill in the art. For example, carboxylate groups activated by carbodiimides can be used or good leaving groups such as para-nitro-phenol can be used. The mass contents of PEG in the final copolymer (XXII) can be between about 5 mass % and about 50 mass %. For copolymer (XXII), this corresponds to molar ratios of the two blocks of leucine/propanediol-succinic acid (A$_1$-C$_1$ blocks) and PEG-diol-succinic acid (B$_3$—C$_1$ blocks) between about 94:6 and about 12:88.

Example 21

Co-poly-{[terephthalyl-bis-(D,L-lactate)-1,4-butylene diamide]$_{81}$-[terphthalyl-bis-(glycolate)-ED600 diamide]$_{19}$} having formula (XXIII) can be synthesized and used in practice of the invention. This copolymer belongs to category (D), type (A$_2$-B$_2$—C$_1$), described above.

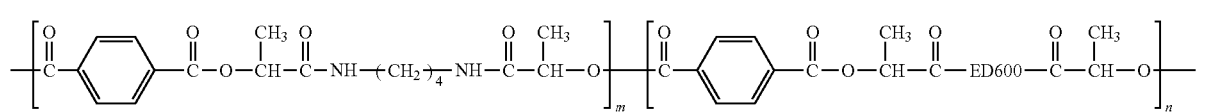

(XXIII)

To synthesize the copolymer (XXIII), the following compounds can be combined in a reaction flask equipped with nitrogen atmosphere, vacuum port, and heating mantle:

(a) about 0.12 g (about $3.5 \times 10^{-4}$ moles) titanium tetrabutoxide;

(b) about 41.2 g (about 0.178 mole) bis-(D,L-lactate)-1,4-butylene diamide;

(c) about 29.83 g (about 0.0417 mole) bis-(glycolate)-ED600 diamide, where(ED-600 is as described above; and (d) about 42.6 g (about 0.219 mole) dimethyl terephthalate.

The flask can be sealed and heated to about 180° C. for about 2 hours. After about 2 hours, the pressure can be reduced to about 0.1 Torr, and the solution can be maintained at about 180° C. for about two more hours.

In this category, only ester bonds present in the copolymer. Amide bonds may, or may not, be present in the reagents. Accordingly, transesterification reactions, under dehydrating conditions, in the presence of the Lewis or Bronsted acid catalysts can be used. Use of acid chlorides is also a viable synthetic technique, because the only hydrolysable bonds that may be present in the reagents are stable amide bonds. The mass contents of PEG in the final copolymer (XXIII) can be between about 5 mass % and about 50 mass %. For copolymer (XXIII), this corresponds to molar ratios of the two blocks of (A$_2$-C$_1$ blocks) (B$_2$—C$_1$ blocks) between about 97:3 and about 49:51.

Example 22

A first composition can be prepared, the composition including:

(a) between about 1.0 mass % and about 15 mass %, for example, about 2.0 mass % co-poly-{[N,N'-sebacoyl-bis-(L-leucine)-1,6-hexylene diester]$_{75}$-[N,N'-sebacoyl-L-lysine benzyl ester]$_{25}$};

(b) between about 0.1 mass % and about 2.0 mass %, for example, about 0.5 mass % paclitaxel; and (c) the balance, a solvent blend of ethanol and 1,1,2-trichloroethane, where the mass ratio between ethanol and 1,1,2-trichloroethane can be about 1:1.

The first composition can be applied onto the surface of bare 12 mm VISION stent (available from Guidant Corporation). Coating can be sprayed and dried to form a drug-polymer layer. A spray coater can be used having a 0.014 round nozzle maintained at ambient temperature with a feed pressure of about 2.5 psi (0.17 atm) and an atomization pressure of about 15 psi (1.02 atm). Coating can be applied at about 20 µg per pass. Between the passes the stent can be dried for about 10 seconds in a flowing air stream at about 50° C. About 270 µg of wet coating can be applied. The stent can be baked at about 50° C. for about one hour, yielding a drug-polymer layer containing about 250 µg of dry coating.

A second composition can be prepared by mixing the following components:

(a) between about 1.0 mass % and about 15 mass %, for example, about 2.0 mass % copolymer (XX) described in Example 18; and (b) the balance, a solvent blend of ethanol and 1,1,2-trichloroethane, where the mass ratio between ethanol and 1,1,2-trichloroethane can be about 1:1.

The second composition can be applied onto the dry drug-polymer layer to form the topcoat layer. The same spraying technique and equipment can be used for the applying the topcoat layer as described for the drug-polymer layer. About 120 µg of wet coating can be applied, followed by drying, e.g., baking at about 50° C. for about one hour, yielding about 100 µg of a biocompatible topcoat layer.

Example 23

A first composition can be prepared by mixing the following components:

(a) between about 1.0 mass % and about 15 mass %, for example, about 2.0 mass % copolymer co-poly-{[N,N'-sebacoyl-bis-(L-leucine)-1,6-hexylene diester]$_{75}$-[N,N'-sebacoyl-L-lysine-4-amino-TEMPO amide]$_{25}$}; and (b) the balance, 100% ethanol.

The first composition can be applied onto the surface of bare 12 mm VISION stent using equipment and coating technique described in Example 22. About 120 µg of wet coating can be applied. The stents can be baked at about 50° C. for about one hour, yielding about 100 µg of a dry primer layer. The copolymer forming the primer layer includes 4-amino-TEMPO (4-amino-2,2',6,6'-tetramethylpiperidine-1-oxy) moiety attached to lysine via an amide linkage.

A second composition can be prepared by mixing the following components:

(a) between about 0.1 mass % and about 3.0 mass %, for example, about 2.0 mass % EVEROLIMUS; and (b) the balance, 100% ethanol.

The second composition can be applied onto the dry primer layer, to form the pure drug layer. The same spraying technique and equipment can be used for the applying the drug layer as described above. Coating can be applied at about 20 µg per pass. Between the passes the stent can be dried for about 10 seconds in a flowing air stream at about 50° C. About 110 µg of neat drug coating can be applied. The stent can be baked at about 50° C. for about one hour, yielding a pure dry drug-layer containing about 100 µg of dry coating.

A third composition can be prepared by mixing the following components:

(a) between about 0.5 mass % and about 10 mass %, for example, about 1.0 mass % copolymer (XX) described in Example 18;

(b) between about 0.5 mass % and about 10 mass %, for example, about 1.0 mass % co-poly-{[N,N'-sebacoyl-bis-(L-leucine)-1,6-hexylene diester]$_{75}$-[N,N'-sebacoyl-L-lysine benzyl ester]$_{25}$} described in Example 22; and (c) the balance, 100% ethanol.

The third composition can be applied onto the dry pure drug layer to form the topcoat layer. The same spraying technique and equipment can be used for the applying the topcoat layer as described above. About 440 µg of wet coating can be applied, followed by drying, e.g., baking at about 50° C. for about one hour, yielding about 400 µg of a biocompatible topcoat layer, which can also control the release of the drug.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate having a coating, the coating including a polymeric product of a reaction between a first reagent and a third reagent and a reaction between a second reagent and a third reagent, wherein:

(a) the first reagent is selected from a group consisting of compounds having formulae (1) and (2):

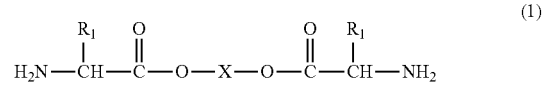

(b) the second reagent is selected from a group consisting of compounds having formulae (5) and (6):

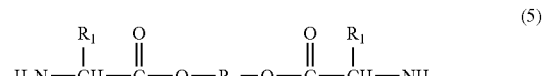

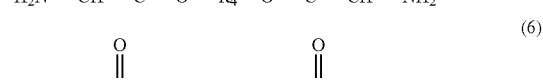

(c) the third reagent is a dicarboxylic acid having the formula (9):

(9)

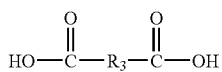

wherein:

R₁ is hydrogen, methyl, iso-propyl, sec-butyl; iso-butyl, or benzyl group;

R₂ is methylene, methyl methylene, n-propylene, iso-propylene, ethylmethylene, n-butylene, iso-butylene, sec-butylene, or n-amylene group;

R₃ is a straight chained or branched aliphatic alkylene group $C_nH_{2n}$, wherein n is an integer between 2 and 12;

PEG is poly(ethylene glycol);

X is a straight chained or branched aliphatic alkylene group $C_nH_{2n}$, wherein n is an integer between 2 and 12; and Y is a straight chained or branched aliphatic alkylene group $C_nH_{2n}$, wherein n is 1, 2, or 5.

2. The medical article of claim 1, wherein the implantable substrate is a stent.

3. A medical article comprising an implantable substrate having a coating, the coating including a polymer selected from the group consisting of copolymers of formulae (23), (24), (26), (27), (28), (29), (35), (40), and (42):

(23)
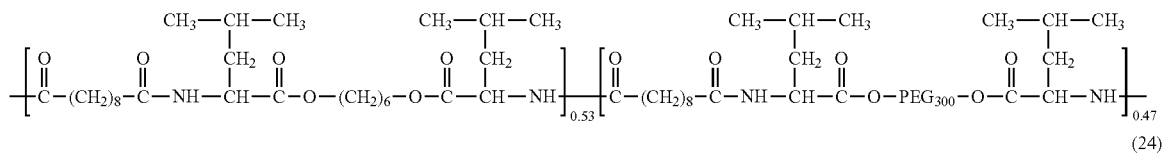

(24)
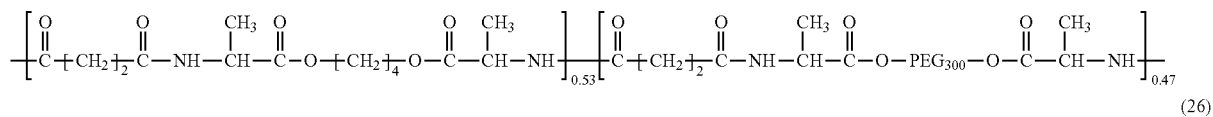

(26)
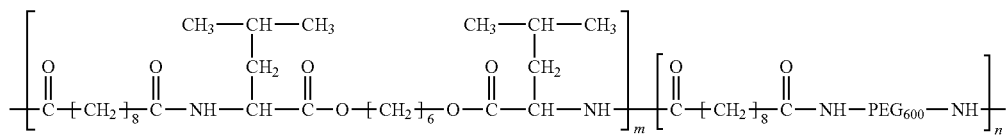

(27)
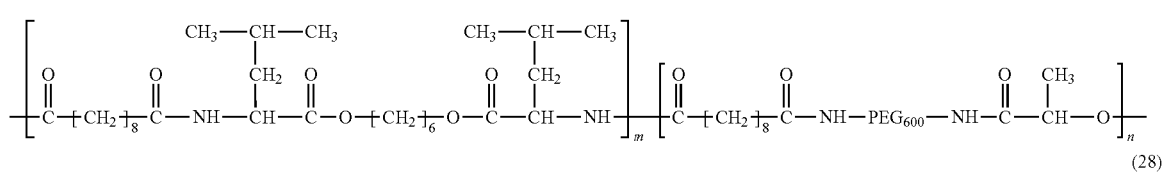

(28)
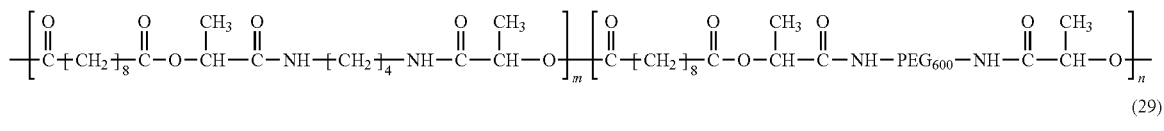

(29)
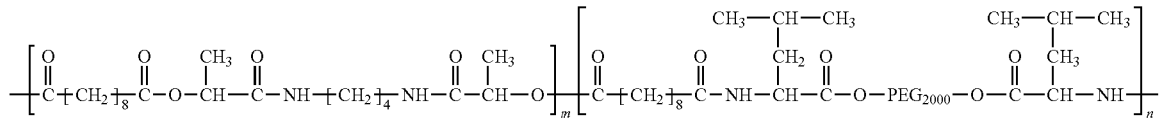

(35)
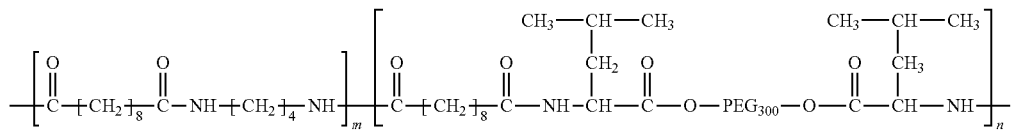

(40)
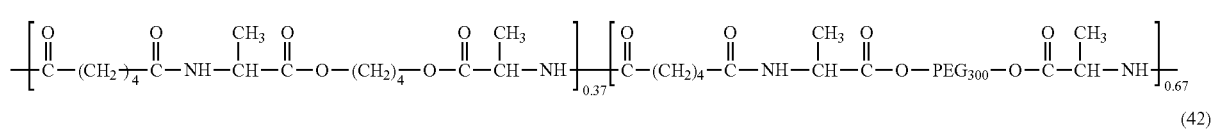

(42)
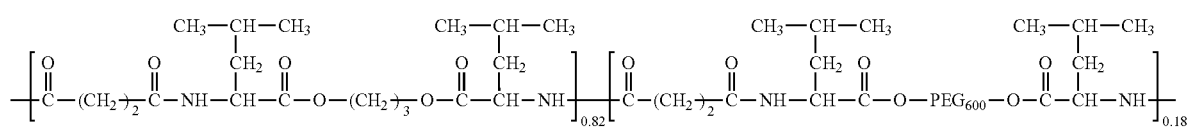

wherein the value of m is between 5 and 1,800, the value of n is between 1 and 800, and the fractional subscripts represent mole fractions.

* * * * *